US008338130B2

(12) United States Patent
Rocha

(10) Patent No.: US 8,338,130 B2
(45) Date of Patent: Dec. 25, 2012

(54) UNIVERSAL FECAL FIXATIVE COMPRISING A LOW MOLECULAR WEIGHT ALCOHOL, A ZINC SALT AND AN ORGANIC ACID

(75) Inventor: Andrew J. Rocha, Long Beach, CA (US)

(73) Assignee: Medical Chemical Corporation, Torrance, CA (US)

( * ) Notice: Subject to any disclaimer, the term of this patent is extended or adjusted under 35 U.S.C. 154(b) by 98 days.

(21) Appl. No.: 13/035,647

(22) Filed: Feb. 25, 2011

(65) Prior Publication Data

US 2012/0219986 A1  Aug. 30, 2012

(51) Int. Cl.
*G01N 1/30* (2006.01)
*A61K 35/36* (2006.01)
*A61K 33/32* (2006.01)

(52) U.S. Cl. .................... 435/40.51; 435/40.5; 424/543; 424/641

(58) Field of Classification Search .......................... None
See application file for complete search history.

(56) References Cited

U.S. PATENT DOCUMENTS

| | | | |
|---|---|---|---|
| 4,493,821 A | 1/1985 | Harrison | |
| 4,666,699 A | 5/1987 | Slifkin | |
| 4,946,669 A * | 8/1990 | Siegfried et al. | 435/40.52 |
| 5,260,048 A | 11/1993 | Ryan | |
| 5,290,706 A | 3/1994 | Camiener | |
| 5,334,509 A | 8/1994 | Riordan | |
| 5,401,625 A * | 3/1995 | Robinson | 435/4 |
| 5,429,797 A | 7/1995 | Camiener | |
| 5,453,381 A | 9/1995 | Lipton | |
| 5,459,073 A * | 10/1995 | Ryan | 436/16 |
| 5,480,613 A | 1/1996 | Riordan | |
| 5,482,676 A | 1/1996 | Camiener | |
| 5,504,012 A | 4/1996 | Lipton | |
| 5,508,175 A | 4/1996 | Slifkin | |
| 5,587,157 A | 12/1996 | Cox et al. | |
| 5,589,164 A | 12/1996 | Cox et al. | |
| 5,607,870 A | 3/1997 | Lipton | |
| 5,622,696 A | 4/1997 | Camiener | |
| 5,736,032 A | 4/1998 | Cox et al. | |
| 5,874,315 A | 2/1999 | Kraft et al. | |
| 5,977,153 A | 11/1999 | Camiener | |
| 6,171,259 B1 | 1/2001 | Fisher | |
| 6,261,788 B1 | 7/2001 | Cummings et al. | |
| 6,596,502 B2 | 7/2003 | Lee | |
| 6,706,290 B1 | 3/2004 | Kajander et al. | |
| 7,368,132 B2 | 5/2008 | Rocha | |
| 7,736,660 B2 | 6/2010 | Elsemore et al. | |
| 2006/0228772 A1* | 10/2006 | Donndelinger | 435/40.5 |
| 2008/0253972 A1* | 10/2008 | Prud'Homme | 424/47 |
| 2010/0248250 A1 | 9/2010 | Tanigami et al. | |

OTHER PUBLICATIONS

Goldman, M., and Brooke, M. Protozoans in Stools Unpreserved and Preserved in PVA-Fixative Public Health Reports, vol. 68, No. 7, (Jul. 1953) pp. 703-706.
Burrows. Improved Preparation of Polyvinyl Alcohol-HgCl2 Fixative Used for Fecal Smears. [online Abstr.], [retrieved on Apr. 18, 2011]. Retrieved from the Internet <URL: http://informahealthcare.com/doi/pdf/10.3109/10520296709114988?journalCode=bih.
Garcia, L.S., Shimizu, R.Y., Brewer, T.C., and Bruckner, D.A. Evaluation of Intestinal Parasite Morphology in Polyvinyl Alcohol Preservative: Comparison of Copper Sulfate and Mercuric Chloride Bases for Use in Schaudinn Fixative. Journal of Clinical Microbiology, vol. 17, No. 6 (Jun. 1983), pp. 1092-1095.
Jensen, B. Comparison of Polyvinyl Alcohol Fixative with Three Less Hazardous Fixatives for Detection and Identification of Intestinal Parasites, Journal of Clinical Microbioloby, Apr. 2000, p. 1592-1598, vol. 38, No. 4 [online]. [retrieved on Feb. 7, 2011]. Retrieved from the Internet < URL: http://jcm.asm.org/cgi/content/full/38/4/1592.
Walsh, J. Problems in Recognition and Diagnosis of Amebiasis: Estimation of the Global Magnitude of Morbidity and Mortality, Reviews of Infectious Diseases, vol. 8, No. 2, Mar.-Apr. 1986 [online], [retrieved on Jan. 11, 2011]. Retrieved from the Internet <URL http://www.jstor.org/pss/4453831.
Garcia, L.S., and Shimizu, R.Y. Evaluation of Intestinal Protozoan Morphology in Human Fecal Specimens Preserved in EcoFix: Comparison of Whealey's Trichrome Stain and EcoStain. Journal of Clinical Microbiology. vol. 36, No. 7 (Jul. 1998), pp. 1974-1976.
Price, D.L. Comparison of Three Collection-Preservation Methods for Detection of Intestinal Parasites. Journal of Clinical Microbiology, vol. 14, No. 6, (Dec. 1981), pp. 656-660.
Dapson, R. W., Glyoxal Fixation: how it works and why it only occasionally needs antigen retrieval. [Online Abstr.], [retrived on Apr. 18, 2011]. Retrieved from the Internet < URL: http:/www.ncbi.nlm.nih.gov/pubmed/17967441.
McLean, I.W., and Nakane, P.K., Periodate-Lysine-Paraformaldehyde Fixative A New Fixative for Immunoelectron Microscopy. vol. 22, No. 12 (May 1974), pp. 1077, 1083.

* cited by examiner

*Primary Examiner* — Mark Shibuya
*Assistant Examiner* — Gary E Hollinden
(74) *Attorney, Agent, or Firm* — Cislo & Thomas, LLP

(57) ABSTRACT

This invention provides compositions and methods for fixing biological samples, particularly fecal samples used in the diagnosis of parasitic infection. The fixative composition of the present invention includes a zinc salt, an organic acid and water and permits staining of biological samples without use of toxic compounds, such as formaldehyde and mercury-containing compounds and without the use of additives such as polyvinyl alcohol. The fixative composition and methods are compatible with many diagnostic assays, including trichrome stains, iron hematoxlin, ELISA, fluorescent assays, and lateral flow assays.

22 Claims, No Drawings

UNIVERSAL FECAL FIXATIVE COMPRISING A LOW MOLECULAR WEIGHT ALCOHOL, A ZINC SALT AND AN ORGANIC ACID

FIELD OF THE INVENTION

The present invention is directed to methods, compositions and kits for collecting and preserving biological specimens, particularly biological specimens derived from parasites in fecal ("stool") samples. The methods compositions and kits permit fixing biological specimens without the need for formaldehyde, formalin, mercury, glutaraldehyde and polyvinyl alcohol.

BACKGROUND

Parasitic infections have a long history of causing disease in humans and animals. These include protozoan parasites such as enteric and extra-intestinal amoebas, toxoplasmas and trichomonas. In addition, other human parasites include helminths such as roundworm, pinworm, hookworm, shisasomes and tapeworms. In general, diagnosis of intestinal parasites is confirmed by staining and microscopically identifying helminth eggs and larvae or protozoan trophozoites and/or cysts in fecal samples. Other assays, such as immunoassays, are also used in diagnosis.

Regardless of the method used, one problem in diagnosing parasitic infections is the delay between collecting and examining specimens, which, without a suitable fixative, results in rapid degradation of the specimen. Short of immediate processing, accurate diagnosis thus depends upon obtaining the best fixation of the specimen upon collection. Fixative solutions are therefore routinely used in processing specimens for parasitic diagnosis.

Fixatives used to preserve stool specimens, however, generally contain mercury, formaldehyde or formalin, which have a number of disadvantages that limit their use. For example, mercury-based fixatives, such as Schaudinn fixative with a mercuric chloride base, generally provide good definition, but present disposal concerns due to the prohibitive cost and the scarcity of disposal companies willing to handle mercury waste. Preservatives comprising formaldehyde or formalin raise similar environmental and health concerns.

In addition, formalin and mercury-based preservatives may limit the techniques that can be used to prepare and analyze the preserved specimens. For example, immunoassays utilizing fluorescent labels may become undetectable when formaldehyde is used and mercury based fixatives, such as Schaudinn's fixative, are not recommended for use in concentration techniques. (see Shimizu, R. Y. (Ed.) "Parasitology" in: *Clinical Microbiology Procedures Handbook*, 3$^{rd}$ ed. Wash. D.C., ASMPress, 2010. p. 9.2.2.3). This presents a problem in that concentration has become a routine procedure as a part of the complete ova and parasite examination and allows the detection of small numbers of organisms that may be missed by using only a direct wet smear (see Id., p. 9.3.4.1). Further, concentrated fecal sediment is recommended for the modified acid-fast and modified trichrome stains used for the *coccidian* and *microsporidia*, respectively (see Id.).

In addition, fixative compositions, even mercury-free fixatives, generally comprise polyvinyl alcohol ("PVA"). PVA is a plastic resin that may serve as a preservative and also serves as an adhesive for the stool material, allowing the stool to adhere to glass microscope slides. PVA, however, also has disadvantages when used in fixative solutions. For example, samples containing some organisms, such as *Trichuris trichiura* (eggs), *Giardia lamblic* (cysts) and *Isospora belli* (oocysts), do not concentrate well from PVA-treated specimens. Also, PVA is generally not compatible with iodine stains, used for direct wet mounts because iodine will cause PVA to coagulate. Further, PVA may cause distortion of ova and larvae morphology and is difficult to prepare in the laboratory (see e.g., Shimizu, R. Y. (Ed.) "Parasitology" in: *Clinical Microbiology Procedures Handbook*, 3$^{rd}$ ed. Wash. D.C., ASMPress, 2010. p. 9.2.2.4); Price, D. L. *Comparison of Three Collection-Preservation Methods Jar Detection of Intestinal Parasites Clin. Microbiology*, Vol. 14, no. 6 (December 1981), p. 656-660).

In addition, glutaraldehyde-based fixative solutions present challenges in terms of costs and storage. Glutaraldehyde is light sensitive and also generally must be stored at sub-zero temperatures, or is at least, refrigerated, to prevent it from polymerizing. Further, glutaraldehyde is generally incompatible with histochemical assays since fixation in glutaraldehyde causes loss of antigenicity. Loss of antigenicity is likely due to the formation of intra- and intermolecular cross-linkages and resulting changes in the tertiary structure of the involved protein (see e.g., McLean, I. W. and P. K. Nakane, *Periodate-Lysine-Paraformaldehyde Fixative A new Fixative for Immunoelectron Microscopy, J. Histochem and Cytochem.*, Vol. 22, no. 12 (1974) pp. 1077-1083).

Although glyoxal aldehyde (1, 2-ethanedione)-based fixatives in some cases may permit selective control over cross-linking (see e.g., Dapson R W, *Glyoxal Fixation: How it Works and Why it Only Occasionally Needs Antigen Retrieved. Biotech. Histochem.*, Vol. 82, no. 3 (January 2007), pp. 161-166), additional processing steps, suitable catalysts, reaction accelerators and/or high pH and high temperatures may be necessary to restore immunoreactivity. For example, glyoxal-based fixatives generally are not compatible with immunoassays for detecting *Giardia* and *Cryptosporidum* infection.

For the foregoing reasons, there is a need for a fixative suitable for fixing biological specimens which 1) do not contain mercury or formaldehyde; 2) are compatible with concentration procedures, permanent staining procedures, latex agglutination, direct and indirect immunofluorescence and enzyme immunoassays; 3) are compatible with different parasitic stages (e.g. cysts, eggs, larvae and trophozoites); and 4) are efficacious without the addition polyvinyl alcohol or the addition of aldehydes such as glyoxal and glutaraldehyde.

SUMMARY

The present invention is directed to compositions, processes (methods) and kits that meet the above-noted needs. The compositions, methods and kits provide mercury-free, formaldehyde-free and PVA-free compositions and methods for fixing biological specimens, particularly fecal samples, for the detection and identification of parasites, including the detection of helminth larvae, eggs, protozoan trophozoites and cysts, coccidian oocysts and microsporidian spores. Specimens processed according to the methods and compositions provided by the invention also do not require the use of mercury, formaldehyde, glyoxal or glutaraldehyde and can be stained by commonly used procedures, including immunoassay procedures, and may be used with "rapid cartridge" products. For example, the universal fixative compositions, methods and kits disclosed herein can be used to perform fecal immunoassays for *Cryptosporidium* spp. and *Giardia lamblia*.

In one aspect of the invention, the basic universal fixative composition of the present invention comprises a zinc salt, preferably an inorganic zinc salt, such as, zinc sulfate; an organic acid such as, for example, acetic acid; alcohol and water. In another embodiment of the invention, the basic universal fixative composition consists essentially of a zinc salt, an organic acid, alcohol and water. In a further embodiment of the invention, the basic universal fixative composition consists of an inorganic zinc salt, an organic acid, alcohol and water. In the preferred embodiment, the alcohols used are low molecular weight alcohols in the range of about 30 to about 65 Daltons and may include methyl alcohol, ethyl alcohol and isopropyl alcohol and mixtures thereof. In the preferred embodiment, the alcohol is preferably reagent alcohol, which comprises about 90% ethyl alcohol, about 5% methyl alcohol and about 5% isopropyl alcohol. The universal fixative of the present invention is compatible with various diagnostic techniques, such as ELISA assays, lateral flow assays, modified Wheatley's Gomorid Trichrome, fluorescent assays, iron hematoxylin stain and concentration procedures.

Preferably, the universal fixative composition comprises from about 1% to about 10% (w/v) of an inorganic zinc salt; from about 20% to about 35% of alcohol, preferably reagent alcohol, (v/v); an organic acid, preferably acetic acid, to a pH of about 3 to about 5, and water Q.S. The sample, for example, a fixed fecal specimen, may then be concentrated through a method comprising filtration and centrifugation. About one drop of the sedimented fecal or other sample is mixed on a microscope slide such that parasites in the sample become detectable by microscopic examination.

The methods and compositions provided by the instant invention also permit PVA-free preparation of microscope slide specimens, which result in the improved adhesion of sample material to the microscope slide without the use of PVA. To prepare slides, the specimen may be centrifuged and the slides prepared from the first centrifugation sediment (without the use of rinse fluids). The slide is preferably dried (e.g. for about two hours in an incubator or overnight at room temperature) and further processing can be carried out without the use of PVA or albumin. Prepared albumin-treated slides may also be used, but if the smear is dried thoroughly before staining, albumin should not be needed. Samples can then be processed according to various diagnostic techniques, such as ELISA assays, lateral flow assays, modified Wheatley's Gomorid Trichrome, fluorescent assays, iron hematoxylin stain and concentration procedures.

These and other features, aspects and advantages of the present invention will become better understood with reference to the following description and claims.

DESCRIPTION OF THE PREFERRED EMBODIMENT(S)

The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

The universal fixative compositions, methods and fixative kits provided by the present invention provide quality fixation without the use of formaldehyde, formalin, mercury, glutaraldehyde or PVA and are compatible with fluorescent assays, immunoassays and stains used in diagnosing parasitic infections. The methods and compositions provided by the present invention also permit the preparation of specimen slides for permanent staining and other procedures without the use of PVA.

Collection of specimens, such as fecal specimens, may be performed according to routine practices known in the art. In one aspect of the invention, the universal fixative composition may comprise from about 0.1% to about 25%, more preferably from about 1% to about 10%, and most preferably from about 4% to about 6% (w/v) of an inorganic zinc salt; from about 1% to about 70%, more preferably from about 10% to about 50%, and most preferably from about 20% to about 35%, of alcohol, preferably reagent alcohol; an organic acid, preferably acetic acid, to a pH of about 1 to about 6, more preferably from about pH 2 to about 5.5, and most preferably from about pH 3 to about 5; and water QS ad (preferably reagent grade water).

In another embodiment of the invention, the universal fixative composition consists essentially of from about 0.1% to about 25%, more preferably from about 1% to about 10%, and most preferably from about 4% to about 6% (w/v) of an inorganic zinc salt; from about 1% to about 70%, more preferably from about 10% to about 50%, and most preferably from about 20% to about 35%, of alcohol, preferably reagent alcohol; an organic acid, preferably acetic acid or other acid to a pH of about 1 to about 6, more preferably from about pH 2 to about 5.5, and most preferably from about pH 3 to about 5; and water QS ad (preferably reagent grade water).

In a further embodiment of the invention, the universal fixative composition consists of from about 0.1% to about 25%, more preferably from about 1% to about 10%, and most preferably from about 4% to about 6% (w/v) of an inorganic zinc salt; from about 1% to about 70%, more preferably from about 10% to about 50%, and most preferably from about 20% to about 35%, of alcohol, preferably reagent alcohol; an organic acid, preferably acetic acid or other acid to a pH of about 1 to about 6, more preferably from about pH 2 to about 5.5, and most preferably from about pH 3 to about 5; and water QS ad (preferably reagent grade water).

The inorganic zinc salt is preferably zinc sulfate, and in the preferred embodiment, is zinc sulfate heptahydrate. Suitable zinc salts also include zinc acetate. In the preferred embodiment, the fixative composition comprises about 5% w/v of zinc sulfate heptahydrate. The acid is preferably an organic acid and, and more preferably is acetic acid. Although addition of acetic acid is preferred to adjust the pH, suitable buffers such as an acetate buffer may also be used. Suitable buffers include buffers having a pKa of about 6. By way of example only, a suitable buffer may comprise from about 2 to about 2.5 grams per liter of sodium acetate, and from about 3.5 to about 4.5 g/l of acetic acid.

A suitable alcohol may comprise ethanol (ethyl alcohol), methyl alcohol (methanol) and/or isopropanol (isopropyl alcohol), or other low molecular weight alcohols. By way of example only, a suitable alcohol solution may comprise a mixture of ethanol, methanol and isopropanol: (1) from about 1% to about 100% of ethanol, more preferably from about 50% to about 95% ethanol, and most preferably about 90% ethanol; (2) from about 1% to about 100% of methyl alcohol, more preferably from about 1% to about 20% methyl alcohol, and more preferably comprises about 5% methyl alcohol; and (3) from about 0% to about 100% of isopropanol, more preferably from about 1% to about 20% isopropanol, and most preferably comprises about 5% isopropanol. In the preferred embodiment, the alcohol used comprises about 100% ethyl alcohol or reagent alcohol (about 90% ethyl alcohol, about 10% methyl alcohol and about 10% isopropyl alcohol) and is present in the fixative composition at about 20% to about 35% of the total volume, and most preferably is about 25% to about 26% of the total volume.

A preferred method of making the universal fixative composition comprises a first step of mixing the zinc salt, preferably zinc sulfate, in sufficient water to dissolve to form a zinc sulfate, or other zinc salt, solution. Next, the alcohol is added to the zinc sulfate, or other zinc salt, solution. The resulting solution may then be pH adjusted to about pH 3 to about pH 5 with, preferably, an organic acid such as acetic acid, or another suitable buffer. The resulting fixative composition is preferably filtered. By way of example only, a 100 ml hatch of the universal fixative composition may be made by combining about 5 g, and more preferably about 4.98 g, of zinc sulfate heptahydrate; about 25-26.5 g, and more preferably about 26.05 g, of reagent alcohol, about 1 g, and more preferably about 1.046 g, of acetic acid and reagent grade water QS ad to 100 ml. By way of example only, a 19 liter batch of the universal fixative composition may be made by combining about 940-950 g, and more preferably about 946 g of zinc sulfate heptahydrate, about 4.5-5 kg, and more preferably about 4.95 kg of reagent alcohol; about 190-200 g, and more preferably about 199 g, of acetic acid and water QS ad to 19 liters.

To use the universal fixative composition provided by the invention, a specimen, such as a fecal sample, or other biological specimen, is collected and placed in an effective amount of universal fixative composition. A preferred ratio of universal fixative composition to sample is preferably from about one part fixative composition to about one part sample, is more preferably about two parts fixative composition to about one part sample, and is most preferably from about three parts of fixative composition to about one part of sample, although other ratios may produce suitable fixation.

For example, a preferred ratio of universal fixative composition to sample may be about 1.0 ml fixative per gram sample, more preferably may be about 2.0 ml fixative per gram of sample, and most preferably may be about 3.0 ml universal fixative composition per gram of sample. The sample may be left in the universal fixative composition for hours, days or may be preserved for months as needed, depending upon the need for evaluation or storage.

After fixation in the universal fixative composition, the specimen may be concentrated as described herein, or by other methods known in the art, and/or may be used to prepare slides for permanent stains using the procedures described herein and/or by other procedures known in the art. Fixed specimens may also be used for diagnostic procedures known in the art. For example, after fixation in the universal fixative provided by the instant invention, the specimen may be used in albumin and/or PVA-free preparation of microscope slide specimens. To prepare slides, the specimen may be centrifuged and the slides prepared from the first centrifugation sediment (without the use of rinse fluids). The slide is preferably dried (e.g. for about two hours in an incubator or overnight at room temperature) and further processing can be carried out without the use of PVA or albumin. Prepared albumin-treated slides may also be used, but if the smear is dried thoroughly before staining, albumin should not be needed. Samples can then be processed according to various diagnostic techniques, such as ELISA assays, lateral flow assays, modified Wheatley's Gomorid Trichrome, fluorescent assays, iron hematoxylin stain and concentration procedures.

The universal fixative composition may be part of a kit comprising a container or receptacle known in the art, preferably a vial (not shown), having a vial body and a visible fill line, preferably on the vial body. Preferably the fill line is disposed on the vial body at a location to assist the operator in adding the sample so that the universal fixative, composition/sample ratio is approximately three to one, or other suitable fixative/sample ratio as may be required. The vial may also comprise a top, closure or a lid comprising a removable "spork" in the lid and fixative composition contained in the vial body. A small sample, for example, of about 1 g to about 5 g, of the specimen may be placed into the body of a vial containing the universal fixative composition. If needed, additional sample may be added until the fluid level reaches the fill line on the vial. The spork may be used to stir and mix the sample with the fixative composition. The operator then may replace the lid on the fixative vial and shake the fixative vial to mix the contents until, preferably, the solution appears homogeneous. The sample is then ready for macroscopic examination and for further processing for direct smears for microscopic examination, permanent stains, concentration procedures, immunoassays and other diagnostic procedures known in the art.

Biological samples processed according to the methods of the present invention are compatible with various diagnostic techniques, including trichrome staining, modified trichrome staining, modified acid fast staining, iron hematoxylin staining, ELISA, lateral flow assays, fluorescent stains and immunoassays.

The universal fixative compositions, methods and kits of the present invention save space and time in that the universal fixative composition can be stored and used directly from a single vial. Also, different types of diagnostic assays may be run with one fixative solution rather than different or multiple solutions for each type of assay. For example, specimens prepared with the universal fixative composition provided the instant invention can be analyzed using various diagnostic techniques, such as ELBA assays, lateral flow assays, modified Wheatley's Gomorid Trichrome, fluorescent assays, iron hematoxylin stain and concentration procedures.

Importantly, the universal fixative compositions, methods and kits of the present invention do not require formaldehyde, formalin or mercury. Also, when using the universal fixative compositions and methods of the instant invention, it is not necessary to include PVA to keep specimens from washing off of the slide.

The following examples illustrate methods for carrying out aspects of the invention and should be understood to be illustrative of, but not limiting upon, the scope of the invention which is defined in the appended claims.

EXAMPLE 1

Collection of Specimens

Fecal specimens for intestinal parasites are preferably collected before the use of any antacids, barium, bismuth, antidiarrheal medication, or oily laxatives. Preferably a minimum of three specimens are collected from the patient on alternate days. Two of the specimens are collected after normal movements, and one after a cathartic, such has magnesium sulfate or fleet Phospho-Soda. Fecal specimens are collected in a clean, dry wide mouthed container, such as a bedpan. Contamination with urine should be avoided. Small samples of the specimen are placed into the vial using the spork built into the lid of the vial. Samples are added to the vial until the fluid level reaches the fill line on the vial to obtain the preferred three to one ratio of universal fixative composition to sample.

The spork is used to stir and mix the sample with the fixative composition. The vial is recapped securely and firmly shaken until the contents are mixed and the solution visually appears homogeneous.

EXAMPLE 2

Examination

The contents of the vial are examined macroscopically for the presence of worms, proglottids and blood. A portion of the fixative composition-treated sample may then be used to prepare direct smears. The smear is prepared by mixing a small amount of preserved sample (approximately 2 mg.) with a drop of physiologic saline on a glass slide. The slide is covered with a coverslip (e.g., 22 mm by 22 mm). The entire coverslip may then immediately be examined using the low power objective. Suspect objects may be examined under high-dry power. With preserved material, the routine ova and parasite examination can begin with the fecal concentration rather than the direct wet mount.

EXAMPLE 3

Concentration

The contents of the fixative vial containing universal fixative composition and sample are mixed thoroughly. The cap is removed from the vial and approximately 8-10 drops of surfactant are added. The vial is recapped and the cap securely fastened. Surfactant is not recommended if the sediment will be used for fluorescent fecal immunoassay. The contents of the vial are then mixed by shaking or vortexine for 30 seconds. A Para-Sed™ (50 ml) or Sed-Connect™ (15 ml) closed fecal concentration system (Medical Chemical Corporation, Torrance, Calif.) is then used for concentration. With the 50 ml centrifuge vial or 15 ml vial still loosely attached to the filter unit, (loose attachment will facilitate the release of air pressure during use), the open end of the filter unit is inserted into the specimen vial until the sealing ring is firmly seated. The 15 ml or 50 ml centrifuge tube is then tightened. If the flow does not start immediately, or the specimen is thick., the flow may be initiated by sharply tapping the centrifuge tube on a counter top. After filtration is complete, the centrifuge tube is tapped on a hard surface, such as the counter top, two or three times to ensure that all the fluid (Para-Sed) or 3-5 ml of material (Sed-Connect) has drained into the tube. The filter unit is then tilted at a slight angle. The concentrator unit and specimen vial are the unscrewed and the vial discarded using established laboratory procedures for fecal specimens. The screw cap is placed on the 50 ml centrifuge tube or push cap on the 15 ml centrifuge tube and centrifuged for approximately 10 minutes at 500×g (1800-2000 rpm for most table top centrifuges). The sample is then decanted and the remaining fixed sediment is mixed with an applicator stick.

If the Para-Sed™ model 695A (Medical Chemical Corporation, Torrance, Calif.) is used, saline is added to the remaining sediment (5% or 10% formalin may also be used) to bring the level of the filtered sediment to the fill line on the Para-Sed™ centrifuge tube. Approximately 3 ml to about 5 ml of ethyl acetate (or other substitute) is added to the tube and the tube is recapped. The tube is then vigorously shaken for thirty seconds. If diethyl ether is used, the cap is carefully loosened after shaking to release the pressure buildup and the cap is then retightened.

The tube is then centrifuged at 500×g for ten minutes. The resulting solution should have four layers. The top layer is ethyl acetate or ethyl ether; the second layer is the debris plug, the third layer is saline or formalin, and the fourth layer is sediment. The debris layer is then ringed with an applicator stick to loosen the debris and the tube inverted to pour off the supernatant fluid and debris layer. While the tube is still inverted, a cotton-tipped applicator is used to clean the sides of the tube, and any ethyl acetate or debris left behind. The sediment at the bottom of the tube will contain the parasites. The remaining sediment is re-suspended with a few drops of 5% or 10% formalin or saline. If the Sed-Connect or Micro-Sed models are used for concentration, the specimen is processed according to the instruction provide with each of those models. Alternately, if none of the above models are available, concentration and permanent slides may be prepared by straining about 2 ml to 3 ml of the sample/fixative composition mixture through gauze into a 15 ml centrifuge tube. The tube is then centrifuged for ten minutes at 500×g. The sediment should be approximately 1 ml in volume. The supernatant fluid is then decanted. The sediment is then mixed and sued for preparing permanent slides or for concentration.

To prepare a wet mount, a sample is taken from the re-suspended material with a capillary or transfer pipette and one or two drops are placed on a microscope slide and covered with a cover slip for examination. Alternately, for an iodine mount, one drop of Lugol's iodine is placed on a slide with one drop of the sample before placing the coverslip. To prepare smears for special or permanent staining, a small sample of the suspended sediment is added to the slide. The sediment can also be used to prepare smears for special staining (modified acid-fast for *coccidia* or modified trichrome for the *microspordia*). The sample is spread over the slide to prepare a thin smear which varies in thickness. The smear is allowed to dry overnight at room temperature, or for several hours (minimum of 30 minutes; 60 minutes if slide is thicker) in a 37 degrees centigrade incubator or slide warmer. The smear will appear opaque when dry. Use of a heating block is not recommended. Albumin may be added to the slide before preparing the stool smear, but should not be needed if the smear is dried thoroughly before staining.

EXAMPLE 4

Trio-Rome Staining Procedure

The slide containing the specimen is placed in Trichrome for six to ten minutes. The slide is then dipped twice in 90% alcohol with 0.5% acetic acid. If the slide appears pale, alcohol without aid may be used or the slide may be stained longer than ten minutes. The slide is then placed in two changes of 100% alcohol for two to five minutes, followed by two changes of xylene (or xylene substitute) for five to ten minutes. The slide is then covered with a coverslip and mounting media.

EXAMPLE 5

Preparation for Immunoassays, Fluorescence and Lateral Flow Procedures

For use with enzyme immunoassay procedures (EIA) and rapid/cartridge/lateral flow procedures (rapid cartridge), the vial containing the sample/fixative composition mixture is left to stand on the counter for at least five minutes before taking the specimen from the top of the vial, without stool particulate material. Protocols known in the art for the particular applicable fecal immunoassay procedure is then followed. For fluorescence procedures (FA), centrifuged samples are used.

EXAMPLE 6

Compatibility of Fixative Composition with Fecal Immunoassay Formats (EIA, FA And Rapid Cartridge)

A minimum of 10 positive specimens (positive for the analyte being tested/*Giardia lamblia* and/or *Cryptosporidium* sp.), 5 negative specimens (no intestinal protozoa or helminths present), and 5 or more specimens (positive with protozoa and/or helminths other than the analyte being tested) were tested using fecal specimens preserved in Universal fixative composition. 100% sensitivity and specificity was found using the following protocol.

Compatibility was confirmed using the following criteria:
A. Positive specimens: All known/confirmed positive *Giardia lamblia* and *Cryptosporidium* specimens were positive in all fecal immunoassay formats tested (EIA, FA, and Rapid Cartridges) according to manufacturers' directions.
B. Negative specimens: All known/confirmed negative specimens containing no *Giardia lamblia* or *Cryptosporidium* sp. gave negative results for each immunoassay format tested following the manufacturers' directions.
C. Positive specimens with other protozoa and/or helminths: All positive specimens with other protozoa and/or helminths tested negative using the fecal immunoassay formats designed to detect *Giardia lamblia* or *Cryptosporidium* (either as single analytes or in combination) according to manufacturers' directions). No cross-reactions with other organisms were found.

EXAMPLE 7

Compatibility of Fixative Composition with Wheatley's Trichrome and Iron Hematoxylin To assess compatibility with routine fecal stains known in the art, 5 each of fixed samples processed according to Wheatley's modification of the Gomori Trichrome stain and Iron Hematoxylin stain were tested.

All known positive specimens containing protozoa and helminth eggs and larvae exhibited normal staining colors and organism morphology (cytoplasm, nucleus, egg structures, larval shapes). Although helminth eggs and larvae are normally identified from the wet concentration mount, occasionally they are seen in stained smears. Representative organisms include: *Entamoeba histolytica/E. dispar, Entamoeba coli, Entamoeba hartmanni, Blastocystis hominis, Endolimax nana, Iodamoeba bütschlii, Dientamoeba fragilis,* and *Giardia lamblia*. Occasional *Trichuris trichlura* and *Ascaris* eggs and *Strongyloides stercoralis* larvae were seen.

Positive specimens preserved in universal fixative composition were also compared with the routine fecal concentration wet mount results using other fixatives. Organism numbers and morphology were compatible; testing was performed on five known positives (protozoan cysts and helminth eggs or larvae). Parasite morphology was excellent (cytoplasm, nuclei count, chromatoidal bodies, egg morphology and helminth larvae internal morphology. Representative organisms would include: *Entamoeba coli, Blastocystis hominis, Iodamoeba bütschlii, Giardia lamblia, Ascaris lumbricoides, Trichuris trichiura, Strongyloides stercoralis, Taenia* spp., hookworm, and *Schistosoma* spp.

Special stains were also tested using positive specimens for coccidia (*Cryptosporidium* spp, *Cyclospora cayetanensis,* and *Cystoisospora belli*) and the microsporidia. 100% sensitivity and specificity was found.

Various Modified Acid-Fast stains were used to stain different coccidia, which had been preserved in universal fixative composition. All known positive specimens tested positive following the standard staining methods, with oocysts being easily visible (5 positives per stain). Negatives (5) did not demonstrate the presence of any oocysts when stained.

Two modified trichrome stains (Weber Green, Ryan Blue) were used to stain microsporidial spores, which has been preserved in universal fixative composition. All known positive specimens tested positive following the standard staining methods, with spores being easily visible (5 positive specimens). Negatives (5) did not demonstrate the presence of any spores when stained.

While the present invention has been described with regards to particular embodiments, it is recognized that additional variations of the present invention may be devised without departing from the inventive concept.

What is claimed is:

1. A mercury-free, formaldehyde-free and polyvinyl alcohol-free universal fixative composition for preserving a fecal sample, said universal fixative consisting essentially of one or more low molecular weight alcohols; zinc sulfate; acetic acid; and water.

2. The universal fixative composition of claim 1, wherein the acetic acid is added in an amount to obtain a pH range of about pH 3 to about pH 5 of the universal fixative composition.

3. The universal fixative composition of claim 1, wherein the zinc sulfate is a heptahydrate.

4. The universal fixative composition of claim 1, wherein the alcohol is selected from the group consisting of ethyl alcohol, methyl alcohol, isopropyl alcohol and mixtures thereof.

5. The universal fixative composition of claim 4, wherein the alcohol is selected from the group consisting of ethyl alcohol and reagent alcohol.

6. The universal fixative composition of claim 1, wherein the alcohol is present in the universal fixative composition at about 20% to about 35% of the total volume of the universal fixative composition.

7. The universal fixative composition of claim 1, wherein the zinc sulfate is present in the universal fixative composition in an amount of about 1% to about 10% w/v.

8. A mercury-free, formaldehyde-free and polyvinyl alcohol-free universal fixative composition for preserving a fecal sample, said universal fixative consisting essentially of: a. one or more low molecular weight alcohols having a molecular weight between about 30 and about 65 Daltons, the total amount of low molecular weight alcohols being in an amount of from about 20% to about 35% of the total volume of the universal fixative; b. about 1% to about 10% w/v of zinc sulfate; c. acetic acid; and d. water; wherein the acetic acid is added in an amount sufficient to adjust the pH of the universal fixative composition to a range from about pH 3 to about pH 5.

9. The universal fixative composition of claim 8, wherein the alcohol is selected from the group consisting of ethyl alcohol, methyl alcohol, isopropyl alcohol and mixtures thereof.

10. The universal fixative of claim 8, wherein the zinc sulfate is about 5% w/v.

11. The universal fixative of claim 8, wherein the zinc sulfate is a heptahydrate.

12. A method for preserving fecal specimens, said method comprising the step of contacting a fecal specimen with an amount of a parasitological fixative effective for preserving the fecal specimen, said parasitological fixative consisting essentially of one or more low molecular weight alcohols; zinc sulfate; acetic acid; and water.

13. The method of claim 12, wherein the zinc sulfate is present in an amount of about 4 to about 6 percent by weight of the parasitological fixative; the alcohol is present in an amount of from about 25 to about 27 percent by weight of the parasitological fixative, and the acetic acid is present in an amount of from about 0.5 to about 1.5 percent by weight of the parasitological fixative.

14. The method of claim 13 wherein the zinc sulfate is about 5 percent by weight of the parasitological fixative.

15. The method of claim 13, wherein the zinc sulfate is a heptahydrate.

16. The method of claim 12, wherein the alcohol is selected from the group consisting of methyl alcohol, ethanol, isopropanol and mixtures thereof.

17. A method for preserving, concentrating and staining fecal specimens being examined for parasites, said method comprising the steps of
  a. contacting a fecal specimen with a parasitological fixative, said fixative comprising from about 4 to about 6 percent by weight of zinc sulfate, from about 25 to about 27 percent by weight of one or more low molecular weight alcohols having a molecular weight between about 30 and 65 Daltons, from about 0.5 to about 1.5 percent by weight of acetic acid, and water;
  b. sedimenting the fecal specimen of step (a) by subjecting the fecal specimen to a method comprising filtration and a single step of centrifugation;
  c. applying a portion of the sedimented fecal specimen obtained from step (b) to a microscope slide after the first centrifugation;
  d. drying the microscope slide prepared in step (c); and
  e. staining said specimen for identification of parasites after step (d).

18. The method of claim 17, wherein the slide is allowed to dry for about two hours in an incubator.

19. The method of claim 17, wherein the slide is allowed to dry for at least about eight hours at room temperature.

20. The method of claim 17, wherein the zinc sulfate is a heptahydrate.

21. The method of claim 17, wherein the alcohol is selected from the group consisting of methyl alcohol, ethanol, isopropanol and mixtures thereof.

22. The method of claim 17, wherein the alcohol is reagent alcohol.

* * * * *